United States Patent [19]
Heil et al.

[11] Patent Number: 5,497,098
[45] Date of Patent: Mar. 5, 1996

[54] MICROWAVE SENSOR FOR IDENTIFYING THE SURFACE PROPERTIES OF A WORKPIECE AND ASSOCIATED METHOD

[75] Inventors: Garret G. Heil, St. Peters; John J. Domalewski, University City; Frederick C. Wear, St. Louis; Stephen C. Buckner, St. Ann; Arthur C. Lind, Chesterfield; Jeffry K. Hoyt, St. Louis, all of Mo.

[73] Assignee: McDonnell Douglas Corporation, St. Louis, Mo.

[21] Appl. No.: 338,007

[22] Filed: Nov. 10, 1994

[51] Int. Cl.[6] .......................... G01R 27/04; G01N 22/00
[52] U.S. Cl. .......................... 324/637; 324/647; 324/717; 343/700 MS
[58] Field of Search .......................... 324/629, 630, 324/632, 631, 637, 638, 639, 644, 647, 693, 717, 332; 343/700 MS

[56] References Cited

U.S. PATENT DOCUMENTS

| | | | |
|---|---|---|---|
| 3,562,642 | 2/1971 | Hohschild | 324/637 X |
| 4,123,703 | 10/1978 | Robinson | 324/632 |
| 5,072,172 | 12/1991 | Stolavczyk et al. | 324/332 |
| 5,334,941 | 8/1994 | King | 324/637 |
| 5,376,889 | 12/1994 | Milroy et al. | 324/632 X |

OTHER PUBLICATIONS

Fact Sheet from Millimeter Wave Technology, Inc., *Microwave Reflectometer Model PR–13* (undated).

Primary Examiner—Kenneth A. Wieder
Assistant Examiner—Diep Do
Attorney, Agent, or Firm—Bell, Seltzer, Park & Gibson

[57] ABSTRACT

A sensor and method for identifying the surface properties of a workpiece includes a microstrip sensor for transmitting and receiving microwave signals and surface properties determining means for determining the surface properties of the workpiece, including the type of material from which the workpiece is constructed, based upon the strength of the detected microwave signals. The surface properties identifying sensor also includes a microwave generator for producing microwave signals at a predetermined frequency for transmission by the microstrip sensor and a detector for detecting the microwave signals received by the microstrip sensor from the workpiece. Thus, workpieces comprised of a conductive material, an insulative material and a conductive material coated with a radar absorbing material can be readily distinguished by the surface properties identifying sensor and method.

18 Claims, 6 Drawing Sheets

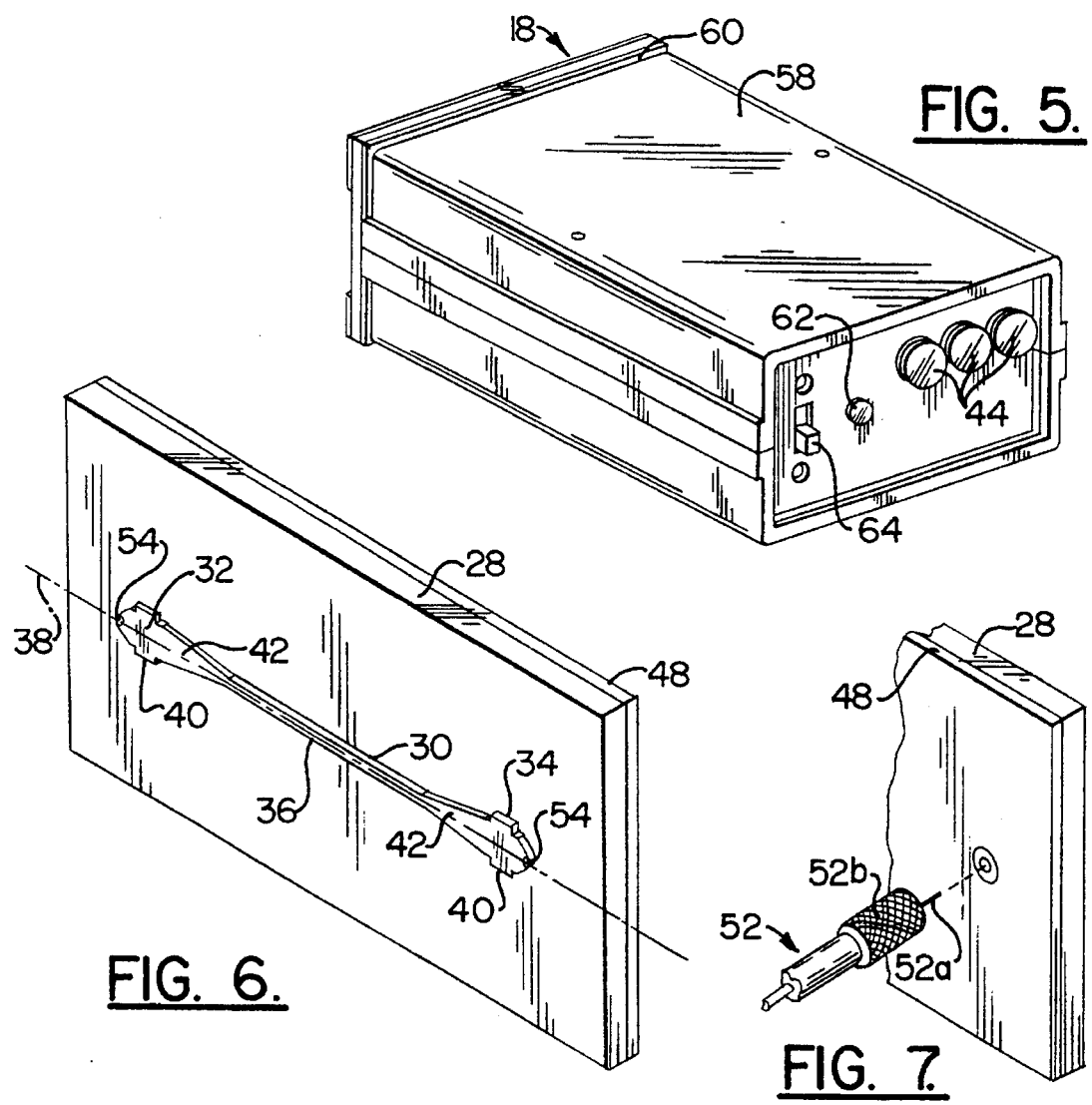

5,497,098

MICROWAVE SENSOR FOR IDENTIFYING THE SURFACE PROPERTIES OF A WORKPIECE AND ASSOCIATED METHOD

GOVERNMENT RIGHTS

The United States Government has rights in this invention pursuant to a contract awarded by the department of the Navy.

FIELD OF THE INVENTION

The present invention relates generally to a sensing method and apparatus and, more particularly, to a method and apparatus for identifying the surface properties of a workpiece.

BACKGROUND OF THE INVENTION

In many instances, it is desirable to identify the surface properties of a workpiece including the type of material from which a workpiece is constructed. Conventionally, a technician could determine the type of material from which a workpiece was constructed and, consequently, the surface properties of the workpiece, by visual inspection of the workpiece. However, workpieces are commonly painted and textured such that workpieces constructed of different types of materials appear visually identical, but have dramatically different surface properties.

For example, some modern military aircraft employ low-observable technology to decrease, or eliminate, the radar signature of the aircraft, thereby significantly increasing the probability of survival of the aircraft on a mission. For example, the surface or skin of the aircraft is typically comprised of a plurality of parts, at least some of which are conductive.

In order to reduce the radar signature of the aircraft, conductive parts are configured so that they do not reflect radar energy to the radar source. In particular, strategically placed radar absorbing coatings cover those parts that would otherwise reflect radar energy to the radar source. During the service life of the aircraft, however, a number of the parts must be periodically replaced. In order to maintain the reduced radar signature of the aircraft, all parts must be replaced with parts which have the same surface properties as the corresponding parts that were removed.

Aircraft, which employ low observable technology to reduce its radar signature during stealth missions, can also be configured for conventional missions in which one or more parts which are coated with Radar Absorbing Material (RAM) during stealth missions are constructed, instead, from other materials, such as metallic or fiberglass materials. These parts, such as door panels, typically appear visually identical to the corresponding parts coated with RAM since, in many instances, the conventional parts are painted the same as the corresponding parts coated with RAM. However, these conventional parts have significantly different electromagnetic properties and, consequently, significantly different effects on the radar signature of the aircraft. Thus, if conventional parts comprised of metallic or fiberglass materials are inadvertently installed on an aircraft intended for a stealth mission, the radar signature of the aircraft will be increased and the probability of survival of the aircraft decreased.

In order to ensure that the parts installed on an aircraft have the proper surface properties for their intended missions, i.e., parts coated with RAM are installed on aircraft configured for stealth missions and parts comprised of more conventional materials, such as metallic or fiberglass materials, are installed on aircraft configured for conventional missions, maintenance crew members can identify the serial number of each part and, based on a tabular listing of the characteristic properties of each part by serial number, identify the type of material forming the part. However, the time and expense required to maintain and update a tabular listing of the characteristics of each part are substantial. In addition, the time required for maintenance crew members to cross-reference each part in the tabular listing is significant and, in an effort to more rapidly launch an aircraft, could be ignored.

Another method to identify that the proper type of parts have been installed on an aircraft is to fly the aircraft, following its initial configuration, in a friendly environment and to observe the radar signature of the plane. By monitoring the radar signature of the aircraft, it can be determined if the proper parts were installed on the aircraft. However, the resulting radar signature of an aircraft would not specifically identify the individual part or parts which were constructed from the improper material. Consequently, maintenance crew members would be required to cross-reference the serial number of each part in order to ensure that the parts constructed of the improper material were replaced. In addition, this method of detecting an improperly configured aircraft is also relatively expensive due to the cost of the diagnostic flight and the time required to observe and analyze the radar signature of the aircraft.

A surface reflectivity sensor is marketed by Millimeter Wave Technology, Inc. which can distinguish between a metal surface and a RAM coated surface. In particular, the surface reflectivity sensor include a pair of antennas which transmit microwave signals to a workpiece and which measure the microwave signals reflected from the workpiece. Based upon the intensity of the reflected microwave signals, the surface reflectivity sensor determines if the workpiece is reflective or absorptive of microwave energy. Based upon the absorption of microwave energy by the workpiece, the surface reflecting sensor can determine if the part is coated with RAM. However, the surface reflectivity sensor cannot distinguish between a RAM coated material and a dielectric material since both materials appear equally reflective to the surface reflectivity sensor. In addition, the surface reflectivity sensor is relatively large and cumbersome since it typically includes a 20–30 pound external power supply. The surface reflectivity sensor also generally requires a 4-inch diameter measurement area so as to inhibit testing of parts having limited lateral access.

SUMMARY OF THE INVENTION

In view of the foregoing background, it is therefore an object to the present invention to provide a relatively inexpensive method and apparatus for rapidly determining the surface properties of a part.

It is also an object of the present invention to provide a method and apparatus for distinguishing between workpieces constructed from conductive materials, insulative materials and RAM.

These and other objects are provided, according to the present invention, by a sensor for identifying the surface properties of a workpiece which includes microstrip sensing means for transmitting microwave signals to and for receiving corresponding microwave signals from the workpiece and a surface properties determining means for determining the surface properties of the workpiece based upon the received microwave signals. Thus, workpieces which have different impedances to the propagation of microwave signals can be distinguished. For example, workpieces constructed of conductive materials, insulative materials and conductive material which are coated with RAM can be distinguished by the surface properties identifying method and apparatus of the present invention.

The surface properties identifying sensor of the present invention also includes a microwave generator, coupled to the microstrip sensing means, for producing microwave signals at a predetermined frequency and a detector means, such as a diode detector, coupled to the microstrip sensing means for detecting the microwave signals received by the microstrip sensing means from the workpiece.

In one embodiment, the microstrip sensing means includes a dielectric substrate, having opposed first and second surfaces, for supporting propagation of microwave signals. The microstrip sensing means also preferably includes a microstrip sensor formed from a layer of conductive material disposed on the first surface of the dielectric substrate for transmitting microwave signals produced by the microwave generator to and for receiving corresponding microwave signals from the workpiece. The microstrip sensor generally includes spaced apart first and second end portions coupled to the microwave generator and the detector means, respectively. In addition, the microstrip sensor preferably includes a center segment extending between and electrically connecting the first and second spaced apart end portions.

The first and second end portions of the microstrip sensor generally have a first predetermined impedance while the center segment generally has a second predetermined impedance. The second predetermined impedance is typically greater than the first predetermined impedance such that microwave signals are transmitted from the center segment to the workpiece. In addition, the microwave generator and the detector each have a third predetermined impedance. Preferably, the first predetermined impedance of the first and second end portions of the microstrip sensor is selected to match the third predetermined impedance to thereby reduce reflections of microwave signals from the microstrip sensor.

According to one embodiment of the present invention, the microstrip sensor extends laterally across the dielectric substrate to thereby define a longitudinal axis. In this embodiment, the respective widths of the first and second end portions, in lateral cross-section, are greater than the width of the central segment, in lateral cross-section, such that the second predetermined impedance of the center segment is greater than the first predetermined impedance of the first and second end portions. Further, the center segment of the microstrip sensor of this embodiment also preferably includes first and second tapered regions adjacent the first and second end portions, respectively. The first and second tapered regions gradually increase the impedance of the center segment from the first predetermined impedance to the second predetermined impedance to further reduce reflections from the microstrip sensor.

The microstrip sensor of one embodiment of the surface properties identifying sensor of the present invention is disposed on a central region of the first surface of the dielectric substrate. The first layer of conductive material comprising the microstrip sensor can also include first and second groundplanes disposed on outlying portions of the first surface of the dielectric sensor in a spaced-apart relationship to the microstrip sensor. The microstrip sensing means can further include a second layer of conductive material disposed on the second surface of the dielectric substrate.

The surface properties identifying sensor also preferably includes an insulating layer disposed on the microstrip sensor. Further, the surface properties identifying sensor can also include a housing to shield the sensor from electromagnetic interference in which the microwave generator, the detector means and the surface properties determining means are disposed. The housing preferably has a relatively small size such that the sensor can be readily carried by an operator in the field.

Thus, by transmitting microwave signals having a predetermined frequency and a predetermined power level to the workpiece and receiving corresponding microwave signals from the workpiece in response to the transmitted microwave signals, workpieces which have different impedances to the propagation of microwave signals can be distinguished. In particular, the received microwave signals are preferably filtered to remove microwave signals having a frequency outside of a predetermined range of frequencies about the predetermined frequency of the transmitted microwave signals produced by the microwave generator.

In addition, the power level of the received microwave signals is preferably compared to high and low predetermined power levels. If the power level of the received microwave signals is greater than the high predetermined power level, the workpiece is constructed of an insulative material. If the power level of the received microwave signals is less than the low predetermined power level, the workpiece is coated with RAM. If, however, the received microwave signal is greater than the low predetermined power level and less than the high predetermined power level, the workpiece is constructed of a conductive material, such as metal.

Based upon the type of material from which the workpiece is constructed, a corresponding output signal is provided to the operator. Thus, the surface properties of the workpiece can be readily determined and workpieces, such as conductive materials, insulative materials and RAM, which have different impedances to the propagation of microwave signals can be distinguished even though such workpieces appear visually identical.

BRIEF DESCRIPTION OF THE DRAWINGS

FIG. 5 is a perspective view of the rear of the surface properties identifying sensor illustrating the indicator lamps and an actuation switch.

FIG. 6 is a perspective view of another embodiment of the microstrip sensing means of the present invention.

FIG. 7 is a perspective view of a portion of the rear surface of the embodiment of the microstrip sensing means of FIG. 6.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Figure 1:
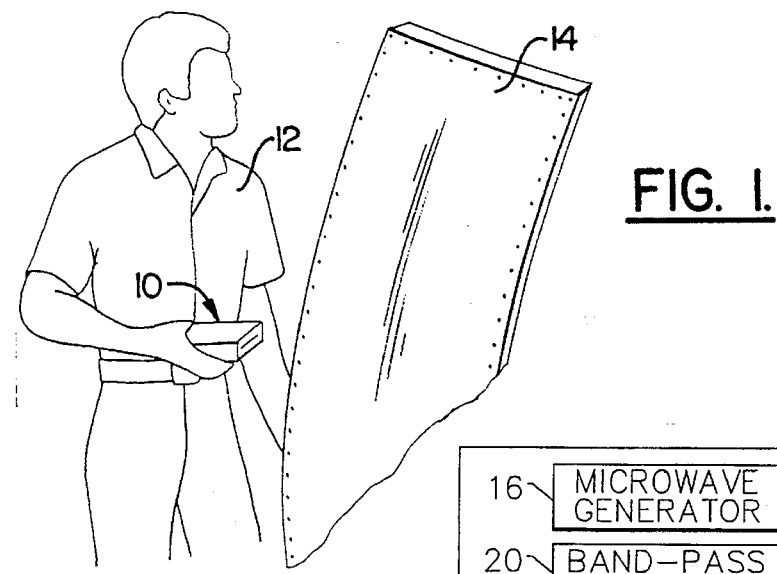
FIG. 1 is a perspective view of an operator utilizing a surface properties identifying sensor of the present invention.

Referring now to FIG. 1, a sensor 10 according to the present invention is employed by a technician 12 to identify the surface properties of a workpiece 14, such as a door panel. As explained in more detail below, workpieces constructed of materials, such as conductive materials, insulative materials and conductive surfaces coated with a radar absorbing material (RAM), which have different impedances to the propagation of microwave signals can be readily distinguished by the surface properties identifying sensor of the present invention.

Figure 2:
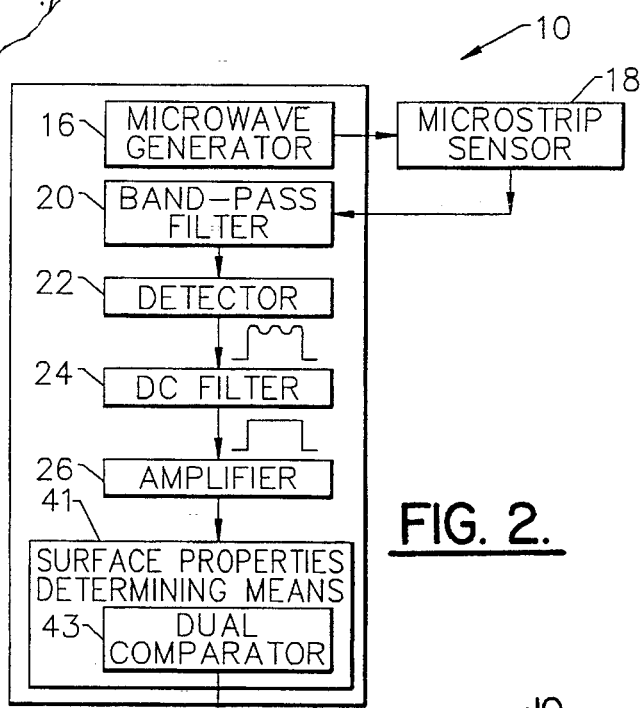
FIG. 2 is a schematic block diagram of the surface properties identifying sensor of the present invention.

As illustrated schematically in FIG. 2, the surface properties identifying sensor 10 includes a microwave generator 16 for producing microwave signals at a predetermined frequency and at a predetermined power level. For example, the microwave generator can include a dielectric resonator oscillator, such as Dielectric Resonator Oscillator No. QTD-1003-AA01 which is manufactured by Quinstar, Inc. The predetermined frequency at which the microwave generator produces microwave signals can be varied without departing from the spirit and scope of the present invention. However, the predetermined frequency is preferably greater than about ten megahertz. For example, microwave signals having predetermined frequencies of ten gigahertz and three gigahertz can be employed. In addition, the predetermined voltage level of the microwave signals can be varied without departing from the spirit and scope of the present invention. For example, microwave signals having a magnitude of between three and five milliwatts, such as those generated by Dielectric Resonator Oscillator No. QTD-1003-AA01 have been successfully employed.

As described in detail below, the surface properties identifying sensor 10 also includes a microstrip sensing means 18, coupled to the microwave generator 16, for transmitting microwave signals produced by the microwave generator to the workpiece 14 and for receiving corresponding microwave signals from the workpiece. The microstrip sensing means is, in turn, coupled to detector means for detecting the microwave signals received by the microstrip sensing means from the workpiece.

As schematically illustrated in FIG. 2, the detector means preferably includes a band-pass filter 20 and a detector 22. The band-pass filter removes received microwave signals which have a frequency outside of a predetermined range of frequencies about the predetermined frequency of the transmitted microwave signals. For example, for a microwave generator 16 which produces microwave signals having a frequency of ten gigahertz, one embodiment of the bandpass filter only passes microwave signals which have a frequency between 9.9 gigahertz and 10.1 gigahertz. Thus, microwave signals which emanate from a source other than the microwave generator of the surface properties identifying sensor 10 are preferably removed by the band-pass filter to thereby further increase the accuracy of the output of the sensor.

The detector 22 receives the filtered output from the band-pass filter 20 and converts the filtered microwave signal into a DC voltage. For example, the detector can be a diode detector such as Diode Detector No. 4506 manufactured by NARDA, Inc. Typically, the DC voltage produced by the diode detector includes an AC ripple component as illustrated in FIG. 2. Thus, the detecting means can also include a DC filter 24 to remove the AC ripple component from the output of the diode detector and to produce a DC voltage representative of the magnitude of the filtered microwave signals received by the microstrip sensing means 18. In some embodiments, the detecting means can also include amplifying means 26, such as an amplifier, for amplifying the DC voltage produced by the DC filter.

The surface properties identifying sensor 10 also preferably includes surface properties determining means 41 which receives the amplified DC signals representative of the filtered microwave signals received by the microstrip sensing means 18 from the workpiece 14. As described in detail below, the surface properties determining means, determines the surface properties of the workpiece, such as the type of material from which the workpiece is constructed, based upon the strength of the detected microwave signals. Thus, workpieces having different impedances to the propagation of microwave signals can be distinguished. In particular, workpieces constructed of conductive materials (such as metals), insulative materials (such as fiberglass), and conductive surfaces coated with RAM can be readily distinguished.

Figure 4:
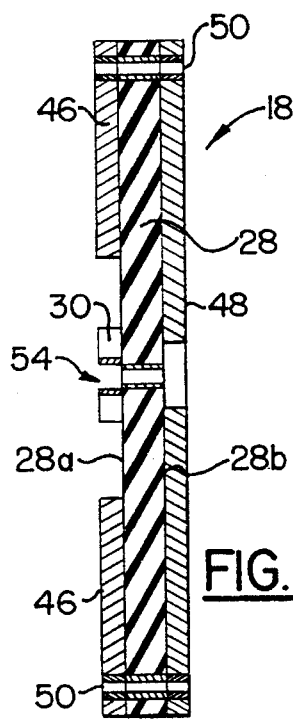
FIG. 4 is a lateral cross-sectional view of the one embodiment of the microstrip sensing means of the present invention taken along line 4—4 of FIG. 3.
Figure 3:
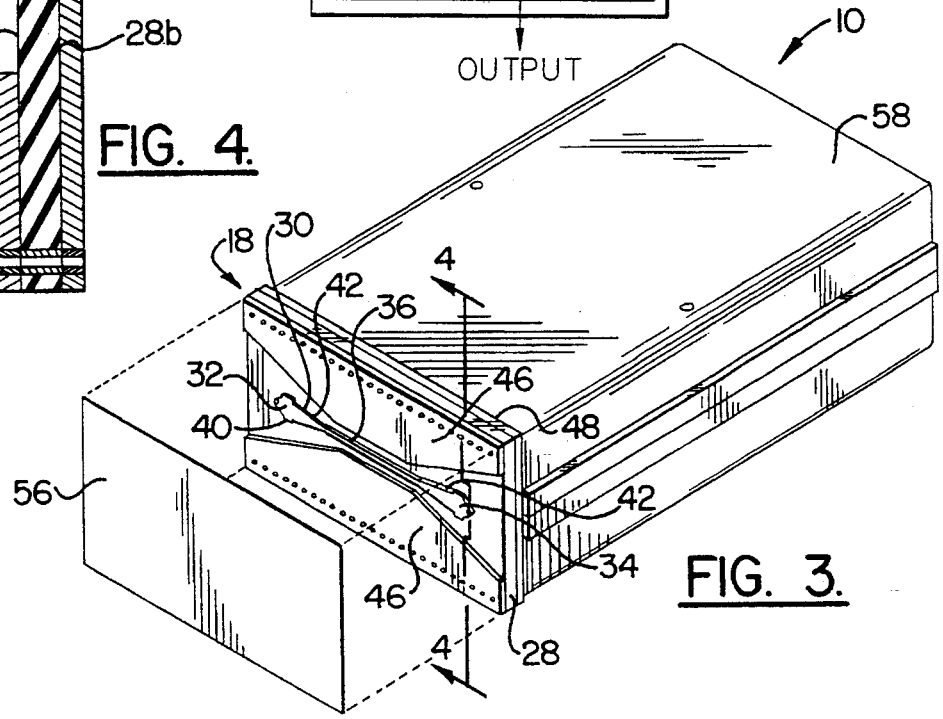
FIG. 3 is a perspective view of the front surface of a surface properties identifying sensor of the present invention illustrating one embodiment of the microstrip sensing means.

As illustrated in FIG. 3 and, in more detail, in FIG. 4, the microstrip sensing means 18 preferably includes a dielectric substrate 28, having first and second opposed surfaces 28a and 28b, for supporting propagation of microwave signals. The dielectric substrate can be comprised of Norplex Oak Grade 605, polyester fiberglass, alumina or ceramic materials, for example. The dielectric substrate preferably has a relatively low dielectric constant, such as less than 4.0, in order to increase the leakage of microwave signals therefrom as described hereinafter. The presence of the workpiece 14 near, and in some embodiments adjacent to, the surface properties sensor 10 influences the signal that travels along center segment 36 from end portion 34 to end portion 32.

The microstrip sensing means also includes a microstrip sensor 30 comprised of a layer of conductive material, such as copper or stainless steel, disposed on the first surface of the dielectric substrate. As shown in FIGS. 3 and 6, the microstrip sensor generally includes spaced-apart first and second end portions 32 and 34 to which the microwave generator and the detector means, respectively, are coupled. The microstrip sensor also generally includes a center segment 36 extending between and electrically connecting the first and second spaced apart end portions.

The first and second end portions 32 and 34 preferably have a first predetermined impedance and the center segment 36 preferably has a second predetermined impedance.

The second predetermined impedance is greater than the first predetermined impedance such that microwave signals are transmitted from the center segment to the workpiece. In addition, the microwave generator 16 and the detector means each preferably have a third predetermined impedance. In order to reduce, if not eliminate reflections, from the microstrip sensor 30, the first predetermined impedance of the first and second end portions of the microstrip sensor is preferably selected to match the third predetermined impedance and, in particular, to match the capacitance and inductance of the microwave generator and detector means. For example, the third predetermined impedance of the microwave generator and the detecting means and, consequently, the first predetermined impedance of the first and second end portions of the microstrip sensor are preferably primarily resistive, such as 50 ohms, for example. Accordingly, the second predetermined impedance of the center segment of the microstrip sensor is preferably greater than 50 ohms, such as approximately 100 ohms, since the increased impedance of the center segment increases the microwave signals transmitted from the center segment to the workpiece 14.

The respective impedances of the first and second end portions 32 and 34 and the center segment 36 of the microstrip sensor 30 are principally determined by the resistivity of the conductive material comprising the microstrip sensor, the size and shape of the first and second end portions and the center segment, and the dielectric properties of the material forming the microstrip sensor. As best illustrated in FIGS. 3 and 6, the microstrip sensor preferably extends across the dielectric substrate 28 to thereby define a longitudinal axis 38. As illustrated, the respective widths of the first and second end portions of this embodiment of the microstrip sensor, in lateral cross-section, are greater than the width of the center segment in lateral cross-section. Thus, since the first and second end portions and the center segment of the microstrip sensor are comprised of the same conductive material and have substantially the same thickness, the impedance of the first and second end portions is, accordingly, less than the impedance of the center segment.

As also illustrated, the first and second end portions 32 and 34 can also include one or more laterally extending wings 40. The size and shape of the wings can be adjusted to more particularly match the first predetermined impedance of the first and second end portions to the third predetermined impedance of the microwave generator 16 and the detector means. For example, the capacitance of the first and second end portions, as determined by the dimensions of the lateral wings 40, serves to provide a matching transition from the third predetermined impedance by cancelling unwanted reflections from end portions 32 and 34.

In order to provide a transition between the first predetermined impedance for the first and second end portions 32 and 34 and the second predetermined impedance of the center segment 36, the center segment preferably includes first and second tapered regions 42 adjacent to first and second end portions, respectively. The first and second tapered regions gradually increase the impedance of the center segment from the first predetermined impedance to the second predetermined impedance. Thus, reflections of microwave signals from the microstrip sensor 30 are further decreased, if not eliminated, by the gradual increase in impedance provided by the first and second tapered regions.

In operation, the microwave signals produced by the microwave generator 16, upon actuation of a switch 64, are coupled to the first end portion 32 of the microstrip sensor 30 and propagate along the microstrip sensor and through the underlying dielectric substrate 28 to the second end portion 34 for detection by the detector means. A portion of the microwave signals propagating along the microstrip sensor are transmitted, however, by the center region 36 of the microstrip sensor. Preferably, the microstrip sensing means is urged against the surface of the workpiece 14 such that the transmitted microwave signals enter the workpiece, as illustrated in block 70 of FIG. 8.

Figure 8:
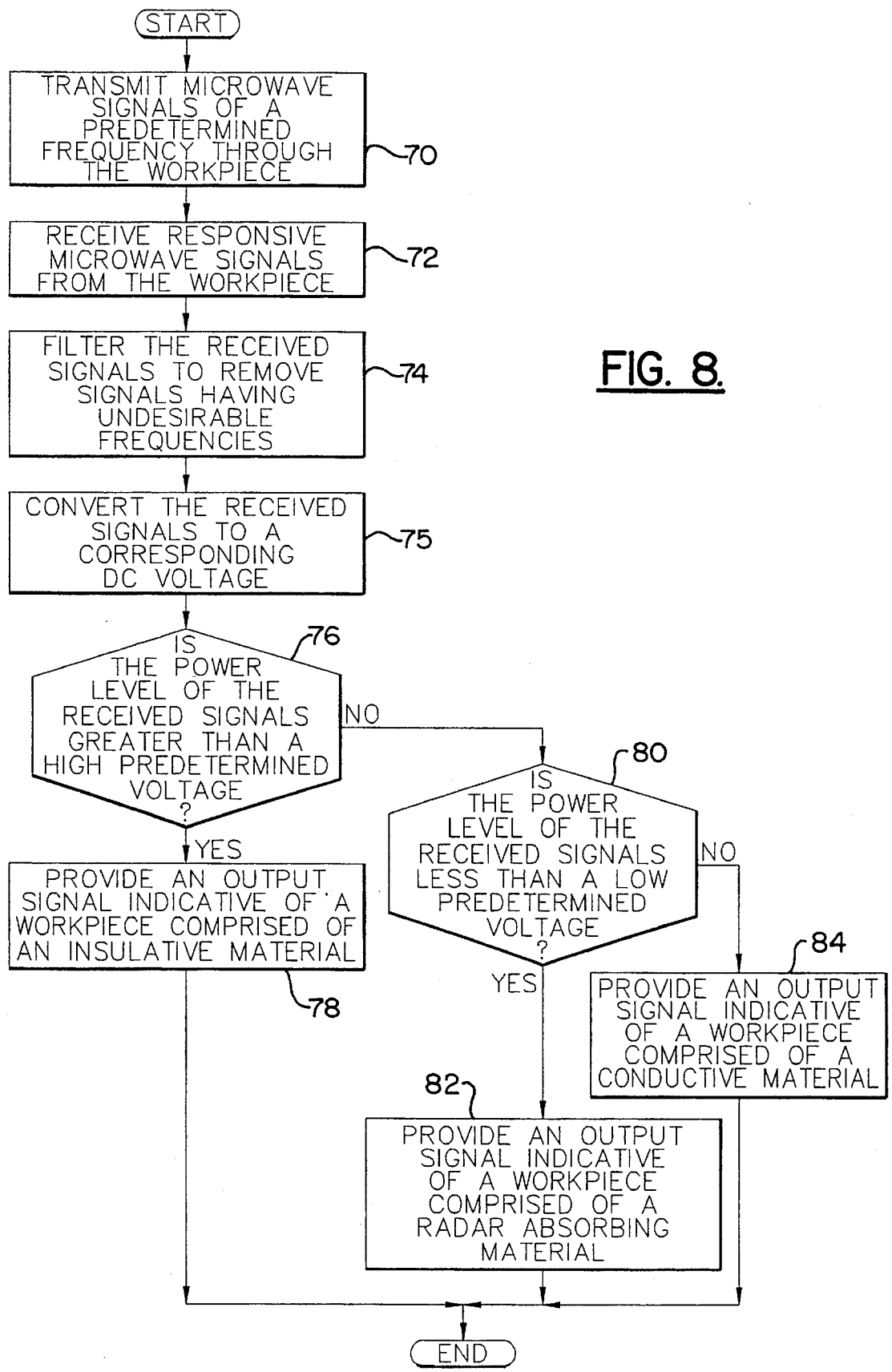
FIG. 8 illustrates detailed operations for identifying the surface properties of a workpiece according to the present invention.

Based upon the surface properties of the workpiece 14, i.e., the type of material from which the workpiece is constructed, corresponding microwave signals are received by the microstrip sensor 30 from the workpiece as shown in block 72 of FIG. 8. For example, workpieces coated with RAM generally absorb the microwave signals such that little, if any, microwave signal is received by the microstrip sensor from the workpiece. Alternatively, if the workpiece is comprised of an insulative material having a relatively low dielectric constant and a relatively low loss factor, such as fiberglass, the microwave signals propagate through the workpiece and are received by the second end portion 34 of the microstrip sensor with little, if any, attenuation. Still further, if the workpiece is comprised of a conductive material, such as metal, the microwave signals are reflected by the conductive material so that the microwave signals received by the detector means are diminished due to interference caused by the reflected microwave signals.

As illustrated schematically in FIG. 2 and described above, the received microwave signals are filtered and converted to a DC voltage which is representative of the magnitude of the received microwave signals, as shown in blocks 74 and 75 of FIG. 8. By comparing the DC voltage level to high and low predetermined voltages, such as with a dual comparator 43, the surface properties of the workpiece 14 and, correspondingly, the type of material forming the workpiece can be determined.

The high and low predetermined power levels are preferably selected based upon the predetermined power level of the microwave signals transmitted by the microwave generator 16 and the amplification of the received microwave signals by the diode detector 22 and the amplifying means 26. Accordingly, DC voltages which are representative of received microwave signals which have been attenuated little, if any, by the workpiece 14 are greater than the high predetermined power level as shown in block 76 of FIG. 8. In these instances, it can be determined that the workpiece is comprised of an insulative material and an appropriate output signal can be provided as shown in block 78 of FIG. 8. Alternatively, DC voltages which are representative of received microwave signals which have been greatly attenuated by the workpiece are less than the low predetermined power level as shown in block 80 of FIG. 8. Thus, it can be determined that the workpiece is comprised of RAM in these instances and an appropriate output signal can be provided as shown in block 82 of FIG. 8. Still further, DC voltages which are representative of received microwave signals which have been somewhat attenuated by the workpiece are greater than the low predetermined power level and less than the high predetermined power level. In these instances, it can be determined that the workpiece is constructed of a conductive material, such as metal, and an appropriate output signal produced as shown in block 84 of FIG. 8.

Based upon the type of material from which it is determined that the workpiece 14 is comprised, an output signal is provided to the technician. For example, as illustrated in FIG. 5, the surface properties identifying sensor 10 can include indicator lamps 44 which are lit according to a predetermined pattern to identify workpieces comprised of conductive materials, insulative materials and RAM, respectively.

As illustrated in FIGS. 3, 4 and 6, the microstrip sensor 30 is preferably disposed on a central region of the first surface 28a of the dielectric substrate 28. In one embodiment of the present invention illustrated in FIG. 3 and in cross-section in FIG. 4, the first layer of conductive material which comprises the microstrip sensor further includes first and second groundplanes 46 disposed on outlying portions of the first surface of the dielectric substrate. Both the first and second groundplanes are spaced apart from the microstrip sensor.

Further, the microstrip sensing means 18 preferably includes a second layer of conductive material 48, such as copper, disposed on the second surface 28b of the dielectric substrate 28, opposite the first surface 28a, as shown in FIGS. 3, 4 and 6. In the embodiment illustrated in FIGS. 3 and 4, the second layer of conductive material and the first and second groundplanes 46 disposed on outlying portions of the first surface are preferably electrically connected via plated-through holes 50 defined along opposed edges of the dielectric substrate. As shown in FIG. 4, the plated-through holes include a layer of conductive material formed on the peripheral walls of the holes. In this embodiment, the second layer of conductive material and, consequently, the first and second groundplanes are typically connected to a reference voltage, such as ground, to further support the propagation of microwave signals along the microstrip sensor 30 and through the dielectric substrate.

Figure 9A:
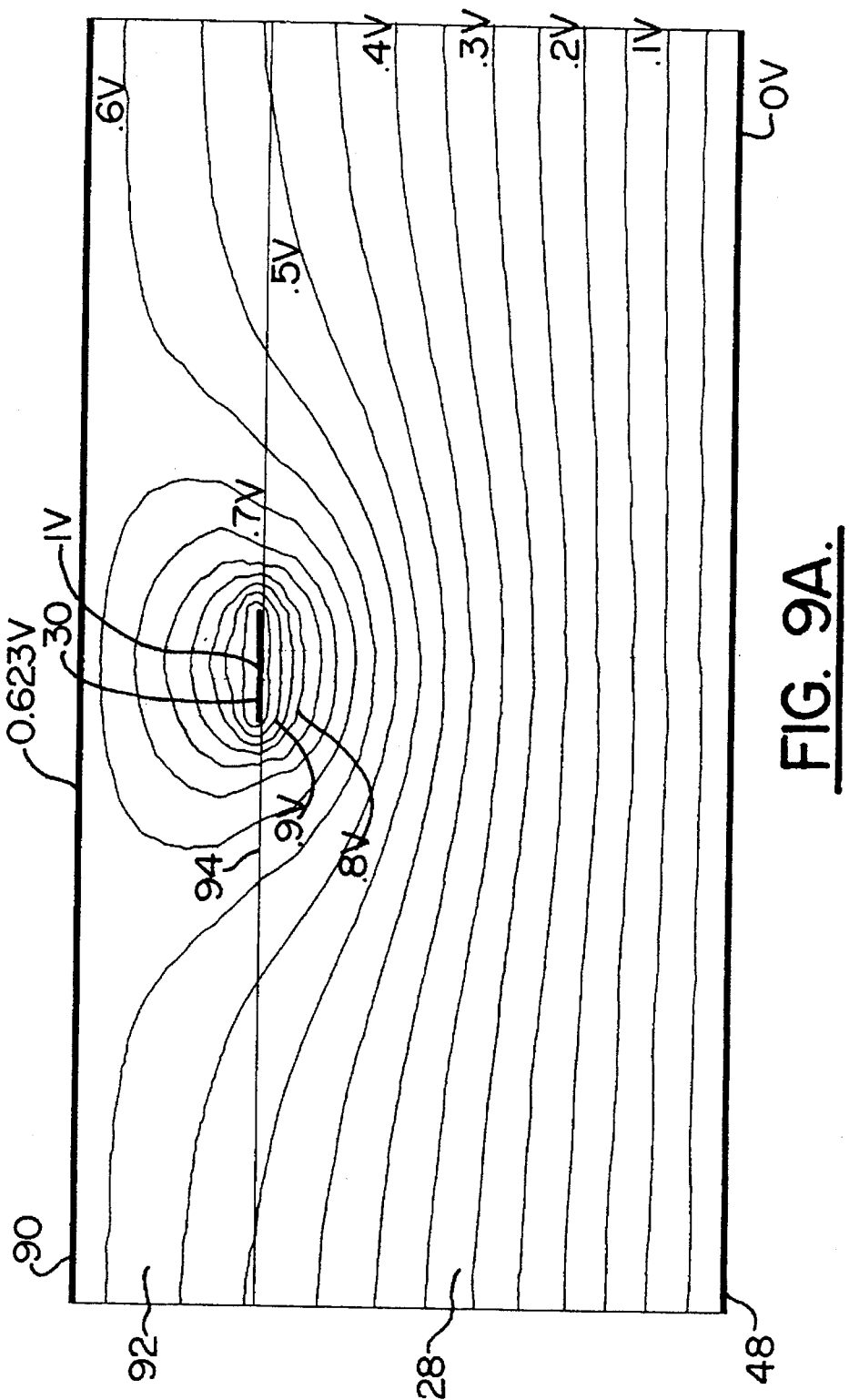
FIGS. 9a–9c illustrate the penetration of the microwave signals generated by the surface properties sensor of the present invention into a workpiece.
Figure 9B:
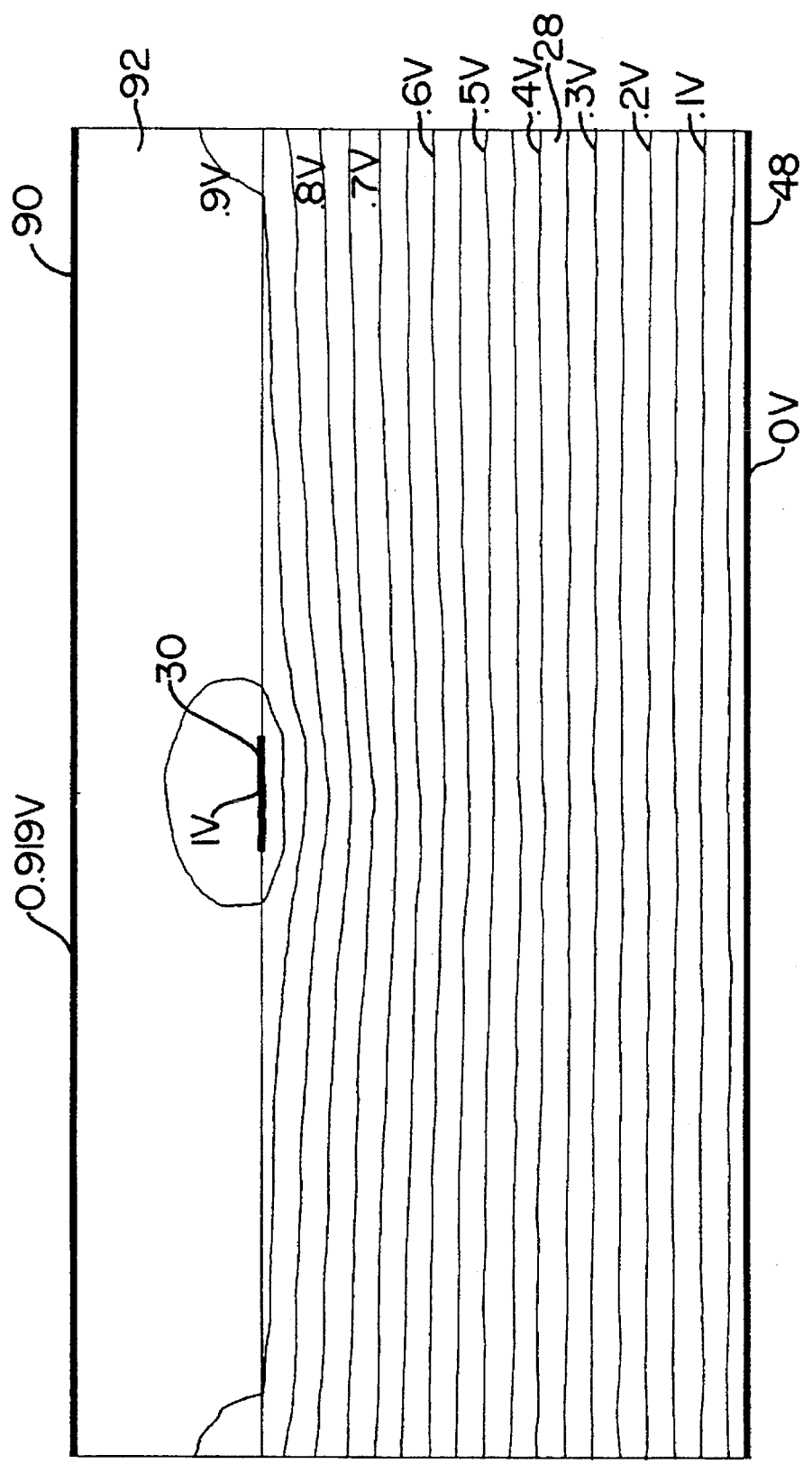

While the microstrip sensing means 18 need not include first and second groundplanes 46, the groundplanes are believed to significantly improve the performance of the sensor 10. In particular, FIGS. 9a and 9b illustrate the voltage levels induced within conductive workpieces 14 by microstrip sensing means which do not include first and second groundplanes. As shown, the sensor 10 contacts the workpiece 14 along a contact plane 94 and establishes different voltage levels within the workpiece, as illustrated by the lines of constant voltage in FIGS. 9a and 9b. For microstrip sensing means which does not include lateral groundplanes, the established voltage levels will vary between workpieces comprised of the same conductive material based upon the dielectric constant of the coating 92 of the workpiece.

For example, in FIG. 9a, the surface 90 of a conductive workpiece 14 which is coated with a material having a relatively low dielectric constant, such as 2 for a TEFLON® coating, is at a significantly lower voltage level than the surface of a conductive workpiece which is coated with a material having a larger dielectric constant, such as 50 for a RAM coating. More specifically, for a microstrip sensor 30 which has a voltage level of 1 volt and which is disposed on a dielectric substrate 28 having a dielectric constant of 2, a workpiece surface coated with a material having a dielectric constant of 2 has a voltage level of 0.623 volts. In contrast, for the same microstrip sensor, a workpiece surface coated with a material having a dielectric constant of 50 has a voltage level of 0.919 volts.

Thus, the voltage levels of the surfaces 90 of conductive workpieces 14 established by a sensor 10 which do not include first and second groundplanes 46 vary based upon the dielectric constant of the coating 92, thereby complicating a study of the surface properties of the workpiece. Further, not only do the voltage levels of the workpiece surfaces vary, but the voltage levels are relatively high, i.e. near the voltage level of the microstrip sensor 30, so as to induce varying radiation patterns which further distort the measurements of the sensor.

Figure 9C:
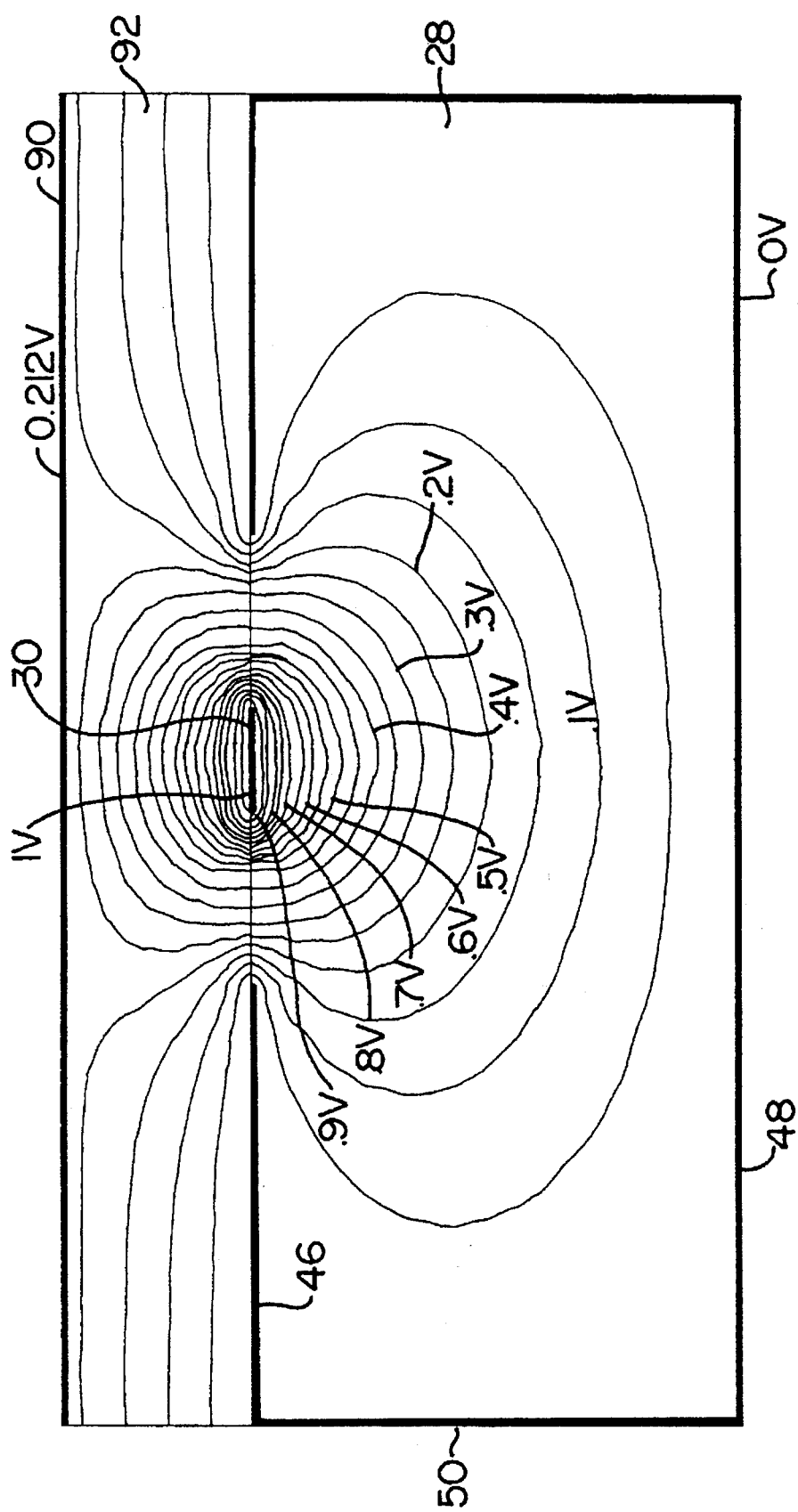

As illustrated in FIG. 9c, the voltage levels established by microstrip sensing means 18 which include first and second groundplanes 46 establish a constant, relatively low voltage on the surface 90 of the workpiece 14 regardless of the dielectric constant of the material coating the workpiece. Accordingly, a quantitative study of the properties of the workpiece can be performed without separately analyzing the properties of the coating 92. In addition, the relatively low voltage level established at the surface of the workpiece, such as 0.212 volts for a reference voltage of 1.0 volts on the microstrip sensor 30, significantly reduces radiation from the workpiece and makes any such radiation constant for workpieces having different coatings so as to further facilitate a quantitative study of various workpieces. As also illustrated in FIG. 9c, the first and second groundplanes principally confine the fields to the regions near the microstrip sensor. Therefore, while the microstrip sensing means 18 need not include first and second groundplanes, the first and second groundplanes are believed to significantly improve the performance of the sensor 10 and the accuracy of its results.

Regardless of the configuration of the microstrip sensor 30, the microwave generator 16 and the detector means can be coupled to the first and second end portions 32 and 34 of the microstrip sensor 30, respectively, via coaxial cables 52 in which microwave signals are conducted by the inner conductor 52a and the outer conductor 52b is held at a reference voltage. As illustrated in FIG. 4, first and second apertures 54 are defined through the dielectric substrate 28 and through the first and second end portions of the microstrip sensor, respectively, to receive the inner conductor of the coaxial cables from the microwave generator and the detector means, respectively. As shown, the peripheral walls of the first and second apertures are also plated with a conductive material so as to electrically connect with the inner conductor of the coaxial cables connecting the microstrip sensor with the microwave generator and the detector means, respectively. Although the microwave generator and detector means are coupled to the microstrip sensor with coaxial cables in the illustrated embodiments, the microwave generator and detector means can be coupled to the microstrip sensor by other means without departing from the spirit and scope of the present invention.

The outer conductor 52b of the coaxial cables 52 connecting the microwave generator 16 and the detector means to the microstrip sensor 30 is preferably electrically connected to the second layer 48 of conductive material disposed on the second surface 28b of the dielectric substrate 28 such that the second layer of conductive material is also held at the reference voltage. In order to prevent electrical connection between the inner and outer coaxial conductors and, accordingly, the microstrip sensor and the second layer of conductive material disposed on the second surface of the dielectric substrate, the second layer of conductive material is spaced a predetermined distance, such as 0.05 inches, from the first and second apertures 54 as shown in FIG. 7.

As described above, the surface properties identifying sensor 10 is preferably positioned adjacent and, more preferably, in physical contact with the workpiece 14. Consequently, the embodiment of the surface properties identifying sensor of FIG. 3 preferably includes an insulating layer 56, typically comprised of a TEFLON® material, disposed on the first layer of conductive material to prevent direct electrical connection between the microstrip sensor 30 and the outlying first and second groundplanes 46 when the surface properties identifying sensor is placed in contact with a workpiece comprised of a conductive material. For clarity, the insulating layer is not illustrated in FIGS. 4, 6 and 7 and is removed from the microstrip sensor in FIG. 3.

As illustrated in FIGS. 1, 3 and 5, the surface properties identifying sensor 10 is preferably relatively small such that a technician 12 can readily carry the sensor in the field. In addition, the surface properties identifying sensor preferably includes a housing 58 shielded from electromagnetic interference in which the microwave generator 16, the detector means and the surface properties determining means are disposed. In order to provide sufficient shielding from electromagnetic interference, the housing can be comprised of a conductive material, such as metal. Alternatively, the housing can be comprised of plastic which is coated with a conductive material. The microstrip sensing means 18 is preferably mounted at a first end of the housing. In order to seal the housing from electromagnetic interfaces, a radio frequency (RF) gasket 60, such as a metal-loaded conductive elastomer seal, is disposed between the microstrip sensing means and the housing. Further, as shown in FIG. 5, the surface properties identifying sensor can also include means, such as a light 62, for indicating that the battery supply is relatively low and should be replaced or recharged.

As described above, the surface properties identifying sensor and method of the present invention can distinguish workpieces 14 having different impedances to the propagation of microwave signals therethrough. Thus, workpieces comprised of conductive material, insulative material and RAM can be reliably and rapidly distinguished. Maintenance crew members can therefore readily determine that the parts that they are installing on an aircraft are appropriate for the type of mission that is planned. For example, a technician can determine that the parts installed on an aircraft which is configured for a stealth mission are, in fact, comprised of RAM, as opposed to a conductive or insulative material which could compromise the radar signature of the aircraft during its mission.

In the drawings and specifications, there has been set forth a preferred embodiment of the invention, and although specific terms are employed, they are used in generic and descriptive sense only and not for purpose of limitation.

That which is claimed is:

1. A sensor for identifying the surface properties of a workpiece, the sensor comprising:

a microwave generator for producing microwave signals at a predetermined frequency;

microstrip sensing means, electrically coupled to said microwave generator, for supporting propagation of the microwave signals produced by said microwave generator from a first end portion toward a second end portion and for transmitting at least a portion of the propagating microwave signals to the workpiece such that the workpiece can influence the strength of the transmitted microwave signals, the second end portion being spaced apart from and electrically connected to the first end portion;

detector means, electrically coupled to the second end portion of said microstrip sensing means, for detecting the propagating microwave signals at the second end of the microstrip sensing means; and surface properties determining means, responsive to said detector means, for determining the surface properties of the workpiece based upon the strength of the detected microwave signals such that workpieces comprised of a conductive material, an insulative material and a conductive material coated with a radar absorbing material can be distinguished.

2. A surface properties identifying sensor according to claim 1 wherein said microstrip sensing means comprises:

a dielectric substrate for supporting propagation of microwave signals, said dielectric substrate having opposed first and second surfaces; and first and second layers of a conductive material disposed on the first and second surfaces of said dielectric substrate, respectively, said first layer comprising a microstrip sensor including the spaced apart first and second end portions wherein said microwave generator is coupled to said first end portion and said detector means is coupled to said second end portion.

3. A surface properties identifying sensor according to claim 2 wherein said microstrip sensor further comprises a center segment extending between and electrically connecting said first and second spaced apart end portions and wherein said first and second end portions have a first predetermined impedance and said center segment has a second predetermined impedance greater than the first predetermined impedance such that the influence of the workpiece on the microwave signals is enhanced.

4. A surface properties identifying sensor according to claim 3 wherein said microwave generator and said detector means each have a third predetermined impedance and wherein the first predetermined impedance of said first and second end portions is selected to match the third predetermined impedance.

5. A surface properties identifying sensor according to claim 4 wherein said microstrip sensor extends laterally across said dielectric substrate to thereby define a lateral axis and wherein the respective widths of said first and second end portions, in lateral cross-section, are greater than the width of said center segment in lateral cross-section such that the impedance of said first and second end portions match the third predetermined impedance.

6. A surface properties identifying sensor according to claim 5 wherein said center segment of said microstrip sensor includes first and second tapered regions adjacent said first and second end portions, respectively, for gradually increasing the impedance of said center segment from the first predetermined impedance to the second predetermined impedance.

7. A surface properties identifying sensor according to claim 2 wherein said microstrip sensor is disposed on a center region of the first surface of said dielectric substrate and wherein said first layer further comprises first and second groundplanes disposed on outlying portions of the first surface of said dielectric substrate in a spaced apart relationship to said microstrip sensor.

8. A surface properties identifying sensor according to claim 2 further comprising an insulating layer disposed on said first layer of conductive material.

9. A surface properties identifying sensor according to claim 1 further comprising a housing shielded from electromagnetic interference in which said microwave generator, said detector means and said surface properties determining means are disposed, said housing having a relatively small size such that the surface properties identifying sensor can be readily carried by an operator.

10. A sensor for identifying the surface properties of a workpiece, the sensor comprising:

a microwave generator for producing microwave signals at a predetermined frequency;

microstrip sensing means comprising:

a dielectric substrate for supporting propagation of microwave signals, said dielectric substrate having opposed first and second surfaces; and a microstrip sensor comprised of a layer of conductive material disposed on the first surface of said dielectric substrate for transmitting microwave signals produced by said microwave generator from a first end portion to a second end portion such that the workpiece can influence the strength of the transmitted microwave signals, wherein the first end portion is coupled to said microwave generator and is spaced apart from the second end portion, and wherein said microstrip sensor further includes a center segment extending between and electrically connecting the first and second spaced apart end portions;

a detector, coupled to the second end portion of said microstrip sensor, for detecting the microwave signals on said microstrip sensor; and surface properties determining means, responsive to said detector means, for determining the surface properties of the workpiece based upon the strength of the detected microwave signals such that workpieces having different impedances to the propagation of microwave signals can be distinguished.

11. A surface properties identifying sensor according to claim 10 wherein said first and second end portions have a first predetermined impedance and said center segment has a second predetermined impedance greater than the first predetermined impedance such that the influence of the workpiece on the microwave signals is enhanced, and wherein said microwave generator and said detector each have a third predetermined impedance which matches the first predetermined impedance of said first and second end portions to reduce reflections of microwave signals therefrom.

12. A surface properties identifying sensor according to claim 11 wherein said microstrip sensor extends laterally across said dielectric substrate to thereby define a lateral axis and wherein the respective widths of said first and second end portions, in lateral cross-section, are greater than the width of said center segment in lateral cross-section such that the impedance of said first and second end portions match the third predetermined impedance.

13. A surface properties identifying sensor according to claim 12 wherein said center segment of said microstrip sensor includes first and second tapered regions adjacent said first and second end portions, respectively, for gradually increasing the impedance of said center segment from the first predetermined impedance to the second predetermined impedance.

14. A surface properties identifying sensor according to claim 10 wherein said microstrip sensor is disposed on a central region of the first surface of said dielectric substrate and wherein said microstrip sensing means further comprises:

a layer of conductive material disposed on the second surface of said dielectric substrate; and first and second groundplanes comprised of a layer of conductive material disposed on outlying portions of the first surface of said dielectric substrate in a spaced apart relationship to said microstrip sensor, said first and second groundplanes being electrically connected to said conductive material layer on the second surface of said dielectric substrate.

15. A surface properties identifying sensor according to claim 10 further comprising an insulating layer disposed on said microstrip sensor.

16. A surface properties identifying sensor according to claim 10 further comprising a housing shielded from electromagnetic interference in which said microwave generator, said detector and said surface properties determining means are disposed, said housing having a relatively small size such that the surface properties identifying sensor can be readily carried by an operator.

17. A method of identifying the surface properties of a workpiece comprising the steps of:

transmitting microwave signals having a predetermined frequency and a predetermined power level to the workpiece;

receiving microwave signals in response to the transmitted microwave signals;

filtering the received microwave signals to remove received microwave signals having a frequency outside of a predetermined range of frequencies about the predetermined frequency of the transmitted microwave signals; and comparing the power level of the received microwave signals, following said filtering step, to high and low predetermined power levels such that workpieces which have different impedances to the propagation of microwave signals can be distinguished.

18. A method according to claim 17 wherein the high predetermined power level is greater than the low predetermined power level and wherein said comparing step comprises the steps of:

determining if the power level of the received microwave signals is greater than the high predetermined power level such that the workpiece is comprised of an insulative material;

determining if the power level of the received microwave signals is less than the low predetermined power level such that the workpiece is comprised of a conductive material coated with a radar absorbing material;

determining if the power level of the received microwave signals is greater than the high predetermined power level and less than the low predetermined power level such that the workpiece is comprised of a conductive material; and providing an output signal indicative of the type of material comprising the workpiece.

* * * * *